United States Patent [19]

Mengel et al.

[11] Patent Number: 4,826,528
[45] Date of Patent: May 2, 1989

[54] HERBICIDALLY EFFECTIVE SULFONYLUREAS

[75] Inventors: Rudolf Mengel, Gau-Algesheim; W. Pfleiderer, Konstanz; Gerbert Linden, Ingelheim am Rhein; Gerhart Schneider, Mühltal, all of Fed. Rep. of Germany

[73] Assignee: Celamerck GmbH & Co. KG., Ingelheim am Rhein, Fed. Rep. of Germany

[21] Appl. No.: 746,971

[22] Filed: Jun. 20, 1985

[30] Foreign Application Priority Data

Jun. 20, 1984 [DE] Fed. Rep. of Germany ....... 3422824

[51] Int. Cl.$^4$ ................... C07D 471/04; A01N 43/90
[52] U.S. Cl. .......................... 71/92; 544/279;
544/320; 71/76; 260/543 R; 260/545 R;
558/49; 558/53; 558/6; 558/48; 560/16; 564/90
[58] Field of Search ................... 544/279, 283, 287;
71/76, 92

[56] References Cited

U.S. PATENT DOCUMENTS

| | | | |
|---|---|---|---|
| 4,333,760 | 6/1982 | Zimmerman | 71/92 |
| 4,509,972 | 4/1985 | Mengel et al. | 71/92 |
| 4,678,502 | 7/1987 | Hanagan et al. | 71/92 |
| 4,723,991 | 2/1988 | Holyoke, Jr. et al. | 544/279 |
| 4,741,760 | 5/1988 | Meyer et al. | 71/92 |
| 4,764,203 | 8/1988 | Töpfl et al. | 71/92 |

Primary Examiner—Donald G. Daus
Assistant Examiner—E. Bernhardt
Attorney, Agent, or Firm—Felfe & Lynch

[57] ABSTRACT

This invention relates to sulfonylureas of the formula

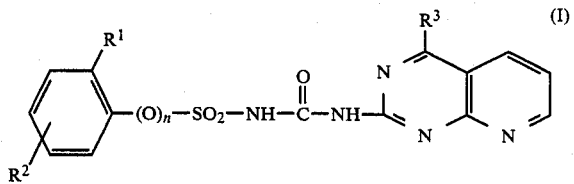

These compounds are useful in killing weeds and in regulating the growth of cultivated plants.

13 Claims, No Drawings

HERBICIDALLY EFFECTIVE SULFONYLUREAS

The invention relates to novel sulfonylureas. More specifically, the invention relates to novel pyrido[2,3-d]pyrimidin-2-yl-sulfonylureas, the preparation thereof, the use of these compounds to combat undesirable plant growth, and novel 2-amino-pyrido[2,3-d]pyrimidines and the synthesis thereof.

It has been found that pyrido[2,3-d]pyrimidin-2-yl-sulfonyl ureas of the formula

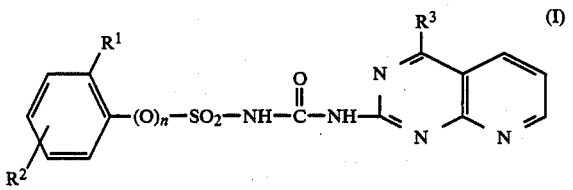

and the salts thereof with acids or bases are herbicidally effective against numerous weeds and wild grasses. Also, these compounds act as growth regulators in some cultivated plants.

In Formula I, n represents 0 or 1;

R$^1$ and R$^2$, which may be identical or different, each represent hydrogen, halogen, cyano, nitro, lower alkoxycarbonyl, optionally halogen-substituted lower alkyl, optionally halogen-substituted lower alkoxy, optionally halogen-substituted lower alkylthio, optionally halogen-substituted lower alkenyl, optionally halogen-substituted lower alkenyloxy, optionally halogen-substituted lower alkenylthio, optionally lower alkyl-substituted cycloalkyl, di(lower alkyl)amino, optionally halogen-substituted cyclopropylmethyl, optionally halogen-substituted cyclopropylmethyloxy, or X—SO$_2$R$^4$, where X represents oxygen, NH, N(lower alkyl), or a direct C-S bond;

R$^3$ represents hydrogen, optionally halogen-substituted lower alkyl, optionally halogen-substituted lower alkoxy, optionally halogen-substituted lower alkylthio, halogen, amino, hydroxyl, mercapto, mono(lower alkyl)amino, or di(lower alkyl)amino; and R$^4$ represents lower alkyl, optionally mono to trihalogen substituted lower alkyl or lower alkoxy, cyclopropyl, methyl, cyclopropylmethoxy, amino, mono(lower alkyl)amino, or di(lower alkyl amino), in free form or in the form of salts with acids or bases.

Special mention should be made of compounds of Formula I wherein n represents 0 or 1;

R$^1$ represents hydrogen, nitro, fluorine, chlorine, lower alkoxycarbonyl, optionally halogen-substituted lower alkyl, optionally halogen-substituted lower alkoxy, optionally halogen-substituted lower alkylthio, optionally halogen-substituted lower alkenyl, optionally halogen-substituted lower alkenyloxy, optionally halogen-substituted lower alkenylthio, optionally halogen-substituted cyclopropylmethyl, optionally halogen-substituted cyclopropylmethyloxy, di(lower alkyl)amino, or X—SO$_2$R$^4$, where X represents oxygen, NH, N(lower alkyl), or a direct C—S bond;

R$^2$ represents hydrogen, chlorine, or fluorine;

R$^3$ represents hydrogen, fluorine, chlorine, lower alkyl, lower alkoxy, lower alkylthio, amino, hydroxyl, mercapto, amino, mono(lower alkyl)amino, di(lower alkyl)amino, or trifluoromethyl; and R$^4$ represents lower alkyl, lower alkoxy, cyclopropylmethoxy, amino, or di(lower alkyl)amino.

Compounds of Formula I wherein n represents 0;

R$^1$ represents methoxycarbonyl, chlorine, or nitro;

R$^2$ represents hydrogen; and

R$^3$ represents amino, methoxy, dimethylamino, methylthio, chlorine, hydroxyl, mercapto, or methylamino, are preferred.

The following compounds of Formula I should be particularly emphasized:

N-(4-aminopyrido[2,3-d]pyrimidin-2-yl)-N'-(2-nitrophenylsulfonyl)-urea

N-(2-chlorophenylsulfonyl)-N'-(4-methoxy-pyrido[2,3-d]pyrimidin-2-yl)-urea

N-(4-aminopyrido[2,3-d]pyrimidin-2-yl)-N'-(2-methoxycarbonylphenylsulfonyl)-urea N-(4-dimethylaminopyrido[2,3-d]pyrimidin-2-yl)-N'-(2-methoxycarbonylphenylsulfonyl)-urea N-(2-methoxycarbonylphenylsulfonyl)-N'-(4-methoxy-pyrido[2,3-d]pyrimidin-2-yl)-urea N-(4-methoxypyrido[2,3-d]pyrimidin-2-yl)-N'-(2-nitrophenylsulfonyl)-urea N-(2-chlorophenylsulfonyl)-N'-(4-chloropyrido[2,3-d]pyrimidin-2-yl)-urea N-(2-methoxycarbonylphenylsulfonyl)-N'-(4-methylthio-pyrido[2,3-d]pyrimidin-2-yl)-urea Within the scope of the above definitions, lower alkyl preferably indicates a linear or branched alkyl group having from 1 to 4 carbon atoms, i.e., methyl, ethyl, n-propyl, isopropyl, n-butyl, sec-butyl, isobutyl, and tert-butyl. This also applies if the lower alkyl group is part of an alkoxy, alkylthio, alkoxycarbonyl, or amino group. Methyl, methoxy, methylthio, methylamino, and dimethylamino should be particularly stressed.

Lower alkenyl groups are preferably linear or branched alkenyl groups containing from 2 to 6 carbon atoms and one or two double bonds. The term includes, by definition, the various Z and E isomers. Particular mention should be made of the vinyl and allyl groups and of the isomeric butenyl and pentenyl groups. This also applies if the lower alkenyl group is part of a lower alkenyloxy or alkenylthio group.

The term halogen refers to fluorine, chlorine, bromine, and iodine, particularly fluorine and chlorine and, to a lesser extent, bromine.

The terms halogen-substituted lower alkyl, lower alkoxy, and lower alkylthio refer to groups wherein the lower alkyl part is defined as above and is substituted with from 1 to 6 halogen atoms which may be identical or different. The trifluoromethyl, trichloromethyl, difluoromethyl, dichloromethyl, fluoromethyl, chloromethyl, bromomethyl, 2,2,2-trifluoroethyl, 2,2,2-trichloroethyl, monochlorodifluoromethyl, and dichloromonofluoromethyl radicals are preferred.

Cycloalkyl groups may be saturated carbocyclic ring systems with a ring size of from three to seven. The cyclopropyl system is preferred.

The terms halogen-substituted lower alkenyl, lower alkenyloxy, and lower alkenylthio refer to groups wherein the lower alkenyl part is defined as above and is substituted with from 1 to 6 halogen atoms which may be identical or different.

The novel compounds of the invention can be prepared in the following ways:

Method A

A phenyl or phenoxysulfonyl isocyanate of the formula

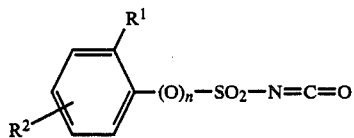

wherein n, $R^1$, and $R^2$ are as hereinbefore defined, is reacted with an amine of the formula

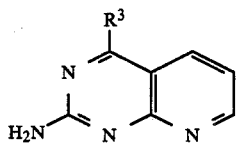

wherein $R^3$ is as hereinbefore defined.

Method B

A carbamate of the formula

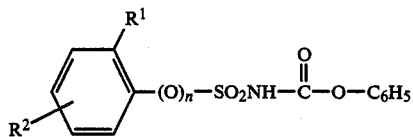

wherein n, $R^1$, and $R^2$ are as hereinbefore defined, is reacted with an amine of Formula III.

Method C

A compound of the formula

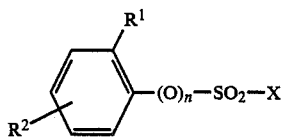

wherein n, $R^1$, and $R^2$ are as hereinbefore defined and X represents halogen, preferably chlorine, is reacted with an imidocarbonate of the formula

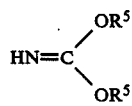

wherein $R^5$ represents a lower alkyl, phenyl, or benzyl group, to obtain an imidocarbonate of the formula

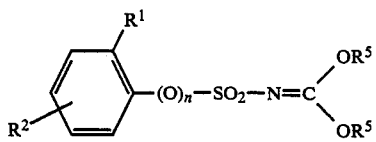

and then with an amine of Formula III. The resultant isourea of the formula

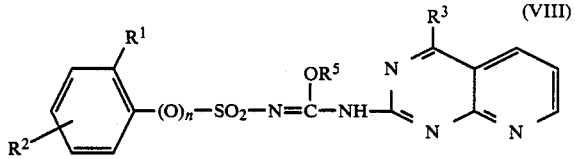

is cleaved with a hydrohalic acid to obtain a urea compound of Formula I.

Method D

A compound of the formula

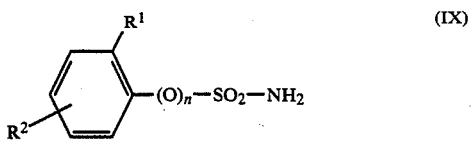

wherein n, $R^1$, and $R^2$ are as hereinbefore defined, is reacted with an amine of Formula III and carbodiimidazole using the process described in German patent application No. 33 46 617, incorporated herein by reference.

If desired, the corresponding base addition salts may be obtained from the compounds of Formula I obtained according to Methods A, B, C, or D by use of suitable alkali or alkaline earth metal compounds or organic bases. This is preferably done by reaction with the calculated quantity of base and isolation of the resulting salt. Moreover, resulting novel compounds according to the invention can, if desired, subsequently be converted into their acid addition salts with inorganic or organic acids. Suitable acids include, for example, hydrochloric acid, hydrobromic acid, sulfuric acid, phosphoric acid, fumaric acid, succinic acid, lactic acid, citric acid, tartaric acid, and maleic acid.

The reaction according to Method A is conveniently carried out in an inert aprotic solvent such as methylene chloride or acetonitrile. The reaction is completed at ambient temperature or at elevated temperature (up to the boiling temperature of the reaction mixture), and the reaction product is isolated and, optionally, purified by conventional methods. Due to the very high reactivity in some cases, particularly in the case of phenoxysulfonyl isocyanates, the reaction should preferably be carried out under anhydrous conditions. The phenoxysulfonyl isocyanates of Formula II needed as starting materials are conveniently prepared using the method described by Lohaus, Chem. Ber. 105, 2791–2799 (1972), incorporated herein by reference. Generally, these compounds do not need to be purified before being further processed.

The phenylsulfonyl isocyanates of Formula II are known or may be prepared analogously to known compounds of this type, e.g., according to German Patent No. 817,602, U.S. Pat. No. 3,379,758, European Patent No. 21,641, German patent application (DE-OS) No. 32 28 101, or Ulrich, Chem. Ber. 65, 369 (1965), all of which are incorporated herein by reference.

The carbamates of Formula IV may be obtained in a manner known per se from the corresponding amides of formula

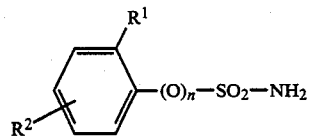

and diphenylcarbonate in the presence of a base. Compounds of Formula IX can be prepared by conventional methods.

Phenoxysulfonyl halides and phenylsulfonyl halides of Formula V, as well as the imidocarbonates of Formula VI, are types of compounds which have long been known.

The 2-aminopyrido[2,3-d]pyrimidines of Formula III required as intermediates are novel with the exception of the two compounds wherein $R^3$=OH or $NH_2$. Thus, the invention also relates to new 2-aminopyrido[2,3-d]pyrimidines of Formula III wherein $R^3$ represents hydrogen, optionally halogen-sub-substituted lower alkyl, optionally halogen-substituted lower alkoxy, optionally halogen-substituted lower alkylthio, halogen, mercapto, mono(lower alkyl)amino, or di(lower alkyl)amino.

Compounds of Formula III wherein $R^3$ represents hydrogen, fluorine, chlorine, lower alkyl, lower alkoxy, lower alkylthio, mercapto, mono(lower alkyl)amino, and di(lower alkyl)amino are preferred.

Particular mention should be made of the compounds of Formula III wherein $R^3$ represents methoxy, dimethylamino, methylthio, chlorine, or mercapto.

Compounds of Formula III may be prepared according to a method known from the literature [Bernetti et al., J. Org. Chem. 27 (1962) 2863, incorporated herein by reference] from the readily obtainable diaminopyrimidines of the formula

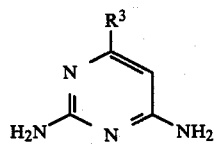

with malonic dialdehyde or derivatives of malonic dialdehyde. Compounds of Formula III wherein $R^3$ represents halogen may be prepared from 2-aminopyrido[2,3-d]pyrimidin-4-ol or 2-aminopyrido[2,3-d]-pyrimidin-4-thiol or may be prepared by the cyclization reaction described hereinbefore, starting from 2,6-diamino-4-chloropyrimidine and 1,1,3,3-tetramethoxypropane.

Furthermore, compounds of Formula III wherein $R^3$ represents mercapto or alkylthio may be prepared from the 4-hydroxy compound using methods known per se with phosphorus pentasulfide, optionally followed by alkylation.

4-Alkylamino or 4-dialkylamino compounds of Formula III may be prepared, for example, by a substitution reaction, starting from the 4-halo or 4-methylthio derivative using methods known per se.

The compounds of Formula I are herbicidally effective. They may be used pre-emergence or post-emergence against numerous weeds and wild grasses, e.g., against monocotyledons: Granineae such as *Echinochloa crus-galli, Alopercurus myosuroides, Avena fatua, Setaria viridis, Digitaria sanguinalis* or Cyperaceae such as *Cyperus esculentus* or dicotyledons: such as *Solanum nigrum, Sinapsis alba, Larium amplexicaule, Centaurea cyanus, Stellaria media, Veronica persicaria, Galium aparine, Matricaria inodora,* and others.

The good selectivity of the novel compounds makes it possible to combat weeds and wild grasses in numerous crops, e.g., in wheat, maize, rice, barley, potatoes, tomatoes, sunflowers, peas, beans, beets, cotton, or soya.

Dependent upon the quantity applied, the compounds of Formula I also have a growth-regulating effect in important cultivated plants such as wheat, barley, and rice. They advantageously alter the shoot structure of these plants without damaging the plant itself. This activity consists mainly of reducing the longitudinal growth of the internodes of the shoot, "stemming" the axis of the shoot. This results in shorter but stronger plants which are less likely to lie flat in the field and can therefore continue to be harvested mechanically without any loss of yield caused by flattened plants.

For use, the compounds of Formula I are processed in a manner known per se with conventional excipients and/or carriers to form the usual formulations, e.g., emulsifiable concentrates or wettable powders, wherein the content of active substance is from about 10 to 95% by weight and which are diluted with water to give the required concentration of active substance for application. However, it is also possible to produce preparations for use in undiluted form, such as granules and dusting powders. In this case, the content of active substance is from about 0.1 to 10% by weight, preferably from about 0.3 to 3% by weight, based upon the total weight of the preparation.

The quantity of active substance applied depends upon the method of application and may vary within wide limits. It ranges from about 1.0 to 1000 gm/ha, preferably from 10 to 500 gm/ha, for herbicidal use. For use in growth regulation, the quantity applied is generally smaller, for example, from about 0.1 to 200 gm/ha, preferably from about 1 to 50 gm/ha.

The following examples are intended to illustrate the invention and should not be construed as limiting the invention thereto.

EXAMPLES

Formulation examples

| Example A - Dusting Composition | |
|---|---|
| Component | % by Weight |
| Compound of Formula I | 0.3 |
| Methyl cellulose | 1.0 |
| Talc | 98.7 |
| | 100.0 |

| Example B - Wettable Powder | |
|---|---|
| Component | % by Weight |
| Compound of Formula I | 25 |
| Kaolin | 55 |
| Colloidal silica | 10 |
| Calcium lignin sulfonate | 9 |
| Sodium tetrapropylene benzenesulfonate | 1 |
| | 100 |

| Example C - Wettable Powder | |
|---|---|
| Component | % by Weight |
| Compound of Formula I | 95 |
| Calcium lignin sulfonate | 4 |
| Sodium tetrapropylene benzenesulfonate | 1 |
| | 100 |

| Example D - Emulsifiable Concentrate | |
|---|---|
| Component | % by Weight |
| Compound of Formula I | 10 |
| Dimethylformamide | 80 |
| Tensiofix AS (emulsifier comprising, available from) | 6.5 |
| Tensiofix DS (emulsifier comprising, available from) | 3.5 |
| | 100.0 |

| Example E - Dispersible Concentrate | | |
|---|---|---|
| Component | | % by Weight |
| Component of Formula I | | 20 |
| Dispersant (e.g., naphthalene sulfate-formaldehyde copolymer-sodium salt) | | 3 |
| BENTONE ® EW (montmorillonite, available from Kronos Titan-GmbH or Riedel) | | 1 |
| Antifoamer (silicon) | | 0.2 |
| Preservative | | 0.05 |
| Water | q.s. ad | 100 |

Spray liquors generally containing from about 0.05 to 0.5% by weight of active substance are prepared from the concentrates of Examples B and D by mixing with water.

In Examples A to E, a compound of Formula I was used as active substance. However, a mixture of two or more compounds of Formula I could instead be used as active substance.

Preparation of Compounds of Formula I and Starting Materials

EXAMPLE 1

N-(4-Amino-pyrido[2,3-d]pyrimidin-2-yl)-N'-(2-nitrophenylsulfonyl)-urea

Amounts of 1.61 gm of 2,4-diaminopyrido[2,3-d]pyrimidine, 2.5 gm of 2-nitrophenylsulfonyl isocyanate, and 100 mg of 1,5-diazabicyclo-(5.4.0)-undec-5-ene are heated to boiling in 40 ml of acetonitrile for four hours with moisture being excluded. The residue is subjected to suction filtration, taken up in 40 ml of boiling glacial acetic acid, and filtered hot. The difficultly soluble residue is washed with hot acetone and dried.

Yield: 2.40 gm (62%) of N-(4-amino-pyrido[2,3-d]pyrimidin-2-yl)-N'-(2-nitrophenylsulfonyl)-urea in the form of colorless crystals, m.p.: 240° C.

Elementary analysis: Calc.: C 43.19 H 2.85 N 25.18. Found: 43.40 3.09 24.98.

EXAMPLE 2

N-(2-Chlorophenylsulfonyl)-N'-(4-methoxypyrido[2,3-d]pyrimidin-2-yl)-urea

A quantity of 1.76 gm of 2-amino-4-methoxypyrido[2,3-d]pyrimidine is added in batches, with stirring and with the exclusion of moisture, to a solution of 2.3 gm of 2-chlorophenylsulfonyl isocyanate in 20 ml of acetonitrile. The reaction mixture readily heats up. It is then stirred for another hour or so. After the addition of ligroin, the precipitate is filtered off, boiled with methanol, and suction filtered while hot.

Yield: 3.6 gm (91%) of N-(2-chlorophenylsulfonyl)-N'-(4-methoxypyrido[2,3-d]pyrimidin-2-yl)-urea in the form of colorless crystals, m.p.: 195° C.

Elementary analysis: Calc.: C 45.75 H 3.07 N 17.7. Found: 45.74 3.09 18.16.

The compounds of Formula I listed in the following table may also be prepared by use of procedures analogous to those of Examples 1 and 2:

TABLE 1

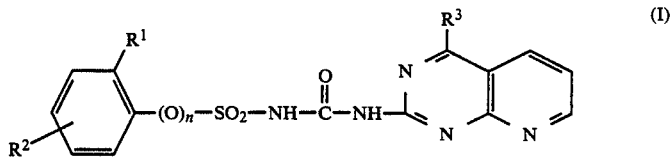

(I)

| Example No. | n | $R^1$ | $R^2$ | $R^3$ | Physical Data |
|---|---|---|---|---|---|
| 3 | 0 | COOCH$_3$ | H | NH$_2$ | M.p.: 220° C. |
| 4 | 0 | COOCH$_3$ | H | N(CH$_3$)$_2$ | M.p.: 182° C. |
| 5 | 0 | COOCH$_3$ | H | N(CH$_2$CH$_3$)$_2$ | — |
| 6 | 0 | COOCH$_3$ | H | OCH$_3$ | M.p.: 192° C. |
| 7 | 1 | COOCH$_3$ | H | NH$_2$ | — |
| 8 | 1 | COOCH$_3$ | H | N(CH$_3$)$_2$ | — |
| 9 | 1 | COOCH$_3$ | H | N(CH$_2$CH$_3$)$_2$ | — |
| 10 | 1 | COOCH$_3$ | H | O—CH$_3$ | — |
| 11 | 0 | COOCH$_3$ | 4-Cl | S—CH$_3$ | — |
| 12 | 1 | COOC$_2$H$_5$ | 4-CH$_3$ | O—CH$_3$ | — |
| 13 | 0 | COOC$_4$H$_9$ | 4-F | Cl | — |
| 14 | 0 | Cl | H | NH$_2$ | M.p.: 240° C. |
| 15 | 0 | Cl | H | N(CH$_3$)$_2$ | — |
| 16 | 0 | Cl | H | CH(CH$_3$)$_2$ | — |
| 17 | 0 | Cl | H | S—CH$_3$ | — |
| 18 | 0 | Cl | 4-CH$_3$ | Cl | — |
| 19 | 0 | F | H | CH(CH$_3$)$_2$ | — |
| 20 | 1 | Cl | H | NH$_2$ | — |
| 21 | 1 | Cl | H | N(CH$_3$)$_2$ | — |
| 22 | 0 | CH$_2$—CH=CH$_2$ | H | NH$_2$ | — |

TABLE 1-continued (I)

$$R^1\text{-}C_6H_3(R^2)\text{-}(O)_n\text{-}SO_2\text{-}NH\text{-}\underset{O}{C}\text{-}NH\text{-}\text{pyrimidine-pyridine}(R^3)$$

| Example No. | n | R¹ | R² | R³ | Physical Data |
|---|---|---|---|---|---|
| 23 | 0 | CH₂—CH=CH₂ | H | OCH₃ | — |
| 24 | 1 | CH₂—CH=CH₂ | 4-CH₃ | Cl | — |
| 25 | 1 | CH₂—CH=CH₂ | 4-Cl | S—CH₃ | — |
| 26 | 0 | CF₃ | H | NH₂ | — |
| 27 | 1 | CF₃ s | H | OCH₃ | — |
| 28 | 0 | CH₂CCl₃ | H | NH₂ | — |
| 29 | 0 | CH₂CCl₃ | H | OCH₃ | — |
| 30 | 0 | C₄H₉ | H | NH—CH₃ | — |
| 31 | 0 | CH₃O | 4-CH₃ | O—CH₃ | — |
| 32 | 0 | CH₃O | H | F | — |
| 33 | 1 | CH₃O | H | F | — |
| 34 | 0 | CH₃S | H | O—CH₃ | — |
| 35 | 0 | CF₃O | H | NH₂ | — |
| 36 | 0 | CF₃O | H | N(CH₃)₂ | — |
| 37 | 0 | CF₃O | H | O—CH₃ | — |
| 38 | 0 | CH₂—CH=CH—CH₃ | H | O—CH₃ | — |
| 39 | 1 | CH₂—CH=CH—CH₃ | H | NH₂ | — |
| 40 | 0 | CH₂—CH=CH—CH₃ | H | NH₂ | — |
| 41 | 0 | N(CH₃)₂ | H | O—CH₃ | — |
| 42 | 0 | CH₂—C(cyclopropyl) | H | O—CH₃ | — |
| 43 | 0 | SO₂CH₃ | H | NH₂ | — |
| 44 | 0 | SO₂OCH₃ | H | O—CH₃ | — |
| 45 | 0 | NHSO₂CH₃ | H | O—CH₃ | — |
| 46 | 1 | NHSO₂CH₃ | H | O—CH₃ | — |
| 47 | 0 | N(CH₃)SO₂CH₃ | H | NH₂ | — |
| 48 | 0 | NHSO₂OCH₂—(cyclopropyl) | H | O—CH₃ | — |
| 49 | 0 | NO₂ | H | N(CH₃)₂ | — |
| 50 | 0 | NO₂ | H | S—CH₃ | — |
| 51 | 0 | NO₂ | H | O—CH₃ | M.p.: 173° C. |
| 52 | 0 | O—CH₂—(cyclopropyl-Cl,Cl) | H | O—CH₃ | — |
| 53 | 0 | O—CH₂—(cyclopropyl-Cl,Cl) | H | N(CH₃)₂ | — |
| 54 | 0 | CH₂—(cyclopropyl-Cl,Cl) | H | O—CH₃ | — |
| 55 | 0 | CH₂—(cyclopropyl-Cl,Cl) | H | N(CH₃)₂ | — |
| 56 | 0 | SO₂NH₂ | H | O—CH₃ | — |
| 57 | 0 | SO₂NHCH₃ | H | O—CH₃ | — |
| 58 | 0 | SO₂N(CH₃)₂ | H | O—CH₃ | — |
| 59 | 0 | OSO₂N(CH₃)₂ | H | N(CH₃)₂ | — |
| 60 | 1 | SO₂NH₂ | H | O—CH₃ | — |
| 61 | 1 | SO₂N(CH₃)₂ | H | N(CH₃)₂ | — |
| 62 | 0 | Cl | H | Cl | M.p.: 155° C. |
| 63 | 0 | COOCH₃ | H | CH₃S | M.p.: 185° C. |
| 64 | 0 | H | H | OCH₃ | — |
| 65 | 0 | H | H | NH₂ | — |
| 66 | 0 | H | H | N(CH₃)₂ | — |

TABLE 1-continued $$\text{(I)}$$

Structure: R¹ and R² substituted phenyl—(O)$_n$—SO$_2$—NH—C(=O)—NH—[pyrido[2,3-d]pyrimidine with R³]

| Example No. | n | R¹ | R² | R³ | Physical Data |
|---|---|---|---|---|---|
| 67 | 0 | H | H | CH(CH$_3$)$_2$ | — |
| 68 | 0 | COOCH$_3$ | H | H | — |
| 69 | 0 | COOCH$_3$ | H | OH | — |
| 70 | 0 | COOCH$_3$ | H | SH | — |
| 71 | 0 | COOCH$_3$ | H | CH$_3$ | — |
| 72 | 0 | Cl | H | CH$_3$ | — |

EXAMPLE 73

2-Amino-4-methoxypyrido[2,3-d]pyrimidine

A quantity of 4.94 gm of 2,4-diamino-6-methoxypyrimidine is heated to boiling in 120 ml of glacial acetic acid and, after the addition of 6.4 ml of 1,1,3,3-tetramethoxypropane, left for a further 45 minutes at boiling temperature. Then, the glacial acetic acid is distilled off and evaporated several times with water, and the residue is taken up in 400 ml of water. After the addition of 5 gm of sodium bicarbonate, the residue is removed by suction filtration and discarded.

The filtrate is extracted several times with chloroform, and the combined extracts are washed with sodium bicarbonate solution and then dried over sodium sulfate.

The residue remaining after evaporation is purified on silica gel with chloroform and a chloroform/methanol mixture and then recrystallized from water.

Yield: 2.5 gm (40.5%) of 2-amino-4-methoxypyrido[2,3-d]pyrimidine in the form of crystals,
m.p.: 178°–180° C.

Elementary analysis Calc.: C 54.54 H 4.58 N 31.80. Found: 54.42 4.56 31.77.

EXAMPLE 74

2-Amino-4-chloro-pyrido[2,3-d]pyrimidine

Starting from 2,6-diamino-4-chloropyrimidine and 1,1,3,3-tetramethoxypropane and using a procedure analogous to that of Example 71, the above compound is isolated after chromatographic purification on silica gel with methanol/diisopropylether (1:1) as a yellow oil which can be used in the following reactions without any further purification.

EXAMPLE 75

2-Amino-4-mercaptopyrido[2,3-d]pyrimidine

2-Amino-4-hydroxypyrido[2,3-d]pyrimidine (8.1 gm) is heated to boiling for ten hours with phosphorus pentasulfide (25 gm) in pyridine (125 ml). After the solvent has been distilled off, the residue is triturated with water, made alkaline with sodium hydroxide solution, and purified with activated charcoal, and the filtrate is acidified with acetic acid. The yellow fine crystalline powder precipitate is washed with water and dried.

2-Amino-4-mercaptopyrido[2,3-d]pyrimidine monohydrate (2.8 gm; 32% yield) is obtained as a yellow powder,
m.p.: 352° C.

EXAMPLE 76

2-Amino-4-methylmercaptopyrido[2,3-d]pyrimidine

2-Amino-4-mercaptopyrido[2,3-d]pyrimidine (1.78 gm; 10 mmol) is dissolved in aqueous potassium hydroxide solution (1.0 gm of KOH in 25 ml of H$_2$O), and 1 ml of methyl iodide is added at ambient temperature with stirring. After 30 minutes' reaction, the precipitated substance is subjected to suction filtration, triturated with a small amount of ethanol, and dried.

2-Amino-4-methylmercaptopyrido[2,3-d]pyrimidine monohydrate (1.8 gm; 86% yield) is obtained as a yellow powder,
m.p.: 180° C.

EXAMPLE 77

2-Amino-4-dimethylamino-pyrido[2,3-d]pyrimidine

2-Amino-4-methylmercaptopyrido[2,3-d]pyrimidine (1.05 gm; 5 mmol) is left in an alcoholic dimethylamine solution (30 ml; 30% dimethylamine in ethanol) at 80° C. for four hours. After the solvent has been distilled off, the residue is triturated with diethylether and removed from the product by suction filtration.

2-Amino-4-dimethylaminopyrido[2,3-d]pyrimidine (1.0 gm; 99% yield), with a melting point of 200° C., is obtained in a virtually quantitative yield.

Herbicidal activity by the pre-emergence method

The plants are sown 2 cm deep in pots, and on the day of sowing they are sprayed with spraying liquor in a quantity of 600 to 800 liters per hectare using a belt-type spray over the surface of the covering soil and then placed in a greenhouse. The activity is determined after three weeks by comparison with an untreated control and given as a percentage (0%—undamaged up to 100%=died off completely). The compounds of Formula I showed good to very good activity. The compound of Example 6 (Table 1) is particularly worth mentioning: its activity on various weeds and wild grasses, applied in a quantity of 0.1 kg/ha, is shown in the following table:

TABLE 2

| Species | Damage/Dying Off (%) |
|---|---|
| *Echinochloa crus-gali* | 86 |
| *Alopecurus myosuroides* | 92 |
| *Avena fatua* | 70 |
| *Setaria viridis* | 98 |
| *Digitaria sanguinalis* | 87 |
| *Solanum nigrum* | 82 |
| *Sinapis alba* | 95 |
| *Lamium amplexicaule* | 98 |
| *Centaurea cyanus* | 88 |
| *Stellaria media* | 96 |

TABLE 2-continued

| Species | Damage/Dying Off (%) |
| --- | --- |
| Veronica persicaria | 99 |
| Galium aparine | 91 |
| Matricaria inodora | 97 |

To demonstrate the effectiveness of compounds of the invention, testing was conducted using the standard commercial sulfonylurea chlorosulfuron[N-2-chlorosulfonyl-N'-(4-methoxy-6-methyl-1,3,5-triazin-2-yl)-urea] on *Cyperus esculentus* as a comparison. The results were as follows:

TABLE 3

| | Damage/Dying Off (%) | |
| --- | --- | --- |
| Quantity applied | Example 6 | Chlorosulfuron |
| 0.2 kg/ha | 99% | 41 |
| 0.1 kg/ha | 97% | 0 |

Herbicidal activity by the post-emergence method

The plants are sown 2 cm deep in pots and cultivated up to the 2.5 leaf stage (monocotyledons/Granineae) or up to the 3–4 leaf state (Cyperus esculentus) or up to the 1.5 successive leaf stage, and then spray liquor is sprayed onto the leaves in a quantity of 600 to 800 liters per hectare using a belt-type spray. The plants are then placed in a greenhouse.

The activity is determined after three weeks by comparison with an untreated control and given as a percentage (0%=undamaged up to 100%=died off completely).

The compounds of Formula I show good to very good activity.

Particular mention should be made of the compound of Example 6 (Table 1), the activity of which on various weeds and wild grasses, when applied in a quantity of 0.1 kg/ha, is as follows:

TABLE 4

| Species | Damage/Dying Off (%) |
| --- | --- |
| Echinochloa crus-galli | 93 |
| Alopecurus myosuroides | 94 |
| Avena fatua | 61 |
| Solanum nigrum | 99 |
| Sinapis alba | 99 |
| Lamium amplexicaule | 99 |
| Centaurea cyanus | 80 |
| Stellaria media | 99 |
| Veronica persicaria | 100 |
| Galium aparine | 98 |
| Matricaria inodora | 97 |

Again, the standard commercial sulfonylurea chlorofulfuron was used on *Cyperus esculentus* as a comparison. The results were as follows:

TABLE 5

| | Damage/Dying Off (%) | |
| --- | --- | --- |
| Quantity applied | Example 6 | Chlorosulfuron |
| 0.2 kg/ha | 94% | 0% |
| 0.1 kg/ha | 90% | 0% |

Growth regulating activity

The growth-regulating activity is determined on treated seeds and after leaf spraying of young plants.

Treatment of seeds

Seeds of wheat and barley are swollen for three hours in solutions of the test substance, rinsed in distilled water, and incubated in the dark in moist vermiculite.

After 12 days the total length of the etiolated seedling is measured.

Leaf spraying

Leaf spraying is carried out analogously to the post-emergence treatment.

The tables below gives the measured length in % as compared to control plants (100%) for seed treatment and leaf spraying, respectively:

TABLE 6

| Compound | Quantity (ppm) | Relative Plant Length (%) | |
| --- | --- | --- | --- |
| | | Wheat | Barley |
| Example 6 | 10 | 83 | 82 |
| Example 6 | 1000 | 47 | 42 |
| Chlorosulfuron | 10 | 100 | 102 |
| Chlorosulfuron | 1000 | 94 | 101 |

TABLE 7

| Compound | Quantity (ppm) | Relative Plant Length (%) | | |
| --- | --- | --- | --- | --- |
| | | Wheat | Barley | Rice |
| Example 6 | 100 | 74 | 68 | 61 |
| Chlorosulfuron | 100 | 99 | 94 | — |

The preceding specific embodiments are illustrative of the practice of the invention. It is to be understood, however, that other expedients knows to those skilled in the art or disclosed herein, may be employed without departing from the spirit of the invention or the scope of the appended claims.

We claim:

1. A compound of Formula I wherein n represents 0 or 1;

$R^1$ and $R^2$, which may be identical or different, represent hydrogen, halogen, cyano, nitro, lower alkoxycarbonyl, lower alkyl, lower alkyl substituted with from 1 to 6 halogen, lower alkoxy, lower alkoxy substituted with from 1 to 6 halogen, lower alkylthio, lower alkylthio substituted with from 1 to 6 halogen, lower alkenyl, lower alkenyl substituted with from 1 to 6 halogen, lower alkenyloxy, lower alkenyloxy substituted with from 1 to 6 halogen, lower alkenylthio, lower alkenylthio substituted with from 1 to 6 halogen, lower cycloalkyl, lower cycloalkyl substituted with from 1 to 6 halogen, di(lower alkyl)amino, cyclopropylmethyl, cyclopropylmethyl substituted with from 1 to 6 halogen, cyclopropylmethoxy, cyclopropylmethoxy substituted with from 1 to 6 halogen, or $X-SO_2R^4$, where X represents oxygen, NH, N(lower alkyl), or a direct C—S bond;

$R^3$ represents hydrogen, lower alkyl, lower alkyl substituted with from 1 to 6 halogen, lower alkoxy, lower alkoxy substituted with from 1 to 6 halogen, lower alkylthio, lower alkylthio substituted with from 1 to 6 halogen, halogen, amino, hydroxyl, mercapto, mono(lower alkyl)amino, or di(lower alkyl)amino; and R⁴ represents lower alkyl, lower alkyl substituted with from 1 to 3 halogen, lower alkoxy, lower alkoxy substituted with from 1 to 3 halogen, cyclopropyl, methyl, cyclopropylmethoxy, amino, mono(lower alkyl)amino, or di(lower alkyl)amino, or an agriculturally acceptable salt thereof with an acid or base.

2. A compound of claim 1, wherein
n represents 0 or 1;
R¹ represents hydrogen, nitro, fluorine, chlorine, lower alkoxycarbonyl, lower alkyl, lower alkyl substituted with from 1 to 6 halogen, lower alkoxy, lower alkoxy substituted with from 1 to 6 halogen, lower alkylthio, lower alkylthio substituted from 1 to 6 halogen, lower alkenyl, lower alkenyl substituted with from 1 to 6 halogen, lower alkenyloxy, lower alkenyloxy substituted with from 1 to 6 halogen, lower alkenylthio, lower alkenylthio substituted with from 1 to 6 halogen, cyclopropylmethyl, cyclopropylmethyl substituted with from 1 to 6 halogen, cyclopropylmethoxy, cyclopropylmethoxy substituted with from 1 to 6 halogen, di(lower alkyl)amino, or X—SO₂R⁴, where X represents oxygen, NH, N(lower alkyl), or a direct C—S bond;
R² represents hydrogen, chlorine, or fluorine;
R³ represents hydrogen, fluorine, chlorine, lower alkyl, lower alkoxy, lower alkylthio, amino, hydroxyl, mercapto, amino, mono(lower alkyl)amino, di(lower alkyl)amino, or trifluoromethyl;
R⁴ represents lower alkyl, lower alkoxy, cyclopropylmethoxy, amino, di(lower alkyl)amino, or an agriculturally acceptable salt thereof with an acid or base.

3. A compound of claim 1, wherein
n represents 0;
R¹ represents methoxycarbonyl, chlorine, or nitro;
R² represents hydrogen; and
R³ represents amino, methoxy, dimethylamino, methylthio, chlorine, hydroxyl, mercapto, or methylamino, or an agriculturally acceptable salt thereof with an acid or base.

4. The compound of claim 1 which is N-(4-aminopyrido[2,3-d]pyrimidin-2-yl)-N'-(2-nitrophenylsulfonyl)-urea.

5. The compound of claim 1 which is N-(2-chlorophenylsulfonyl)-N'-(4-methoxypyrido[2,3-d]pyrimidin-2-yl)-urea.

6. The compound of claim 1 which is N-(4-aminopyrido[2,3-d]pyrimidin-2-yl)-N'-(2-methoxycarbonylphenylsulfonyl)-urea.

7. The compound of claim 1 which is N-(4-dimethylaminopyrido[2,3-d]pyrimidin-2-yl)-N'-(2-methoxycarbonylphenylsulfonyl)-urea.

8. The compound of claim 1 which is N-(2-methoxycarbonylphenylsulfonyl)-N'-(4-methoxypyrido[2,3-d]pyrimidin-2-yl)-urea.

9. The compound of claim 1 which is N-(4-methoxypyrido[2,3-d]pyrimidin-2-yl)-N'-(2-nitrophenylsulfonyl)-urea.

10. The compound of claim 1 which is N-(2-chlorophenylsulfonyl)-N'-(4-chloropyrido[2,3-d]pyrimidin-2-yl)-urea.

11. The compound of claim 1 which is N-(2-methoxycarbonylphenylsulfonyl)-N'-(4-methylthiopyrido[2,3-d]pyrimidin-2-yl)urea.

12. A herbicidal or growth-regulating composition which comprises a herbicidally or growth-regulatingly effective amount of one or more compounds of claim 1 together with a carrier.

13. The composition of claim 12 wherein the carrier comprises an extender or surface-active substance.

* * * * *